United States Patent [19]
Junino et al.

[11] Patent Number: 4,891,045
[45] Date of Patent: Jan. 2, 1990

[54] 2,4-DIAMINO-1,3,5-TRIMETHOXYBENZENE, PROCESS FOR ITS PREPARATION AND ITS USE AS A COUPLER IN OXIDATION DYES FOR KERATINOUS FIBRES

[75] Inventors: Alex Junino, Livry-Gargan; Jean J. Vandenbossche, Aulnay-sous-Bois; Herve Borowiak, Tremblay-les-Gonesse; Gerard Lang, Saint-Gratien, all of France

[73] Assignee: L'Oreal, Paris, France

[21] Appl. No.: 212,318

[22] Filed: Apr. 27, 1988

[30] Foreign Application Priority Data

Jun. 25, 1987 [LU] Luxembourg .................. 86931

[51] Int. Cl.$^4$ .................. A61K 7/13; C07C 91/40; C07C 91/42
[52] U.S. Cl. .................. 8/411; 8/405; 8/408; 8/412; 8/416; 8/424; 8/435; 8/407; 564/443
[58] Field of Search .................. 564/443; 8/411, 412, 8/416, 424, 407, 408

[56] References Cited

U.S. PATENT DOCUMENTS 4,566,876 1/1986 Brown et al. .................. 8/411

FOREIGN PATENT DOCUMENTS 2542193 9/1984 France.

Primary Examiner—Paul Lieberman
Assistant Examiner—John F. McNally
Attorney, Agent, or Firm—Cushman, Darby & Cushman

[57] ABSTRACT

The invention relates to 2,4-diamino-1,3,5-trimethoxybenzene, a process for its preparation by catalytic reduction of 2,4-dinitro-1,3,5-trimethoxybenzene, and to its use, as a coupler, in combination with at least one oxidation dye precursor of the para type, for dyeing keratinous fibres and particularly human hair.

The hair dyeing compositions according to the invention contain, in a cosmetically acceptable aqueous substrate, 0.05 to 3.5% by weight of 2,4-diamino-1,3,5-trimethoxybenzene or one of its salts, which imparts strong blue colors to hair when it is combined with p-phenylenediamines, or red colors when it is combined with p-aminophenols, in an alkaline oxidizing medium.

21 Claims, No Drawings

2,4-DIAMINO-1,3,5-TRIMETHOXYBENZENE, PROCESS FOR ITS PREPARATION AND ITS USE AS A COUPLER IN OXIDATION DYES FOR KERATINOUS FIBRES

The present invention relates to 2,4-diamino-1,3,5-trimethoxybenzene as a new compound, a process for its preparation and its use as a coupler, in combination with oxidation dye precursors for dyeing keratinous fibres and in particular human hair.

It is known that it is commonplace, in dyeing keratinous fibres such as human hair or furs, to employ dye compositions containing oxidation dye precursors and in particular para-phenylenediamines and ortho- or paraaminophenols, which are generally referred to by the name of oxidation bases.

It is also known that colour modifiers or couplers, and in particular aromatic meta-phenylenediamines, metaaminophenols and meta-diphenols are employed in order to vary the shades obtained with these oxidation bases.

In the alkaline oxidizing media which are usually employed in oxidation dyeing, para-phenylenediamines and para-aminophenols give rise to coloured indamines or indoanilines in the presence of couplers such as meta-phenylenediamines.

The indamines formed from meta-phenylenediamines and from para-phenylenediamines in an alkaline oxidizing medium, and more particularly in the presence of hydrogen peroxide, impart very strong blue colours to keratinous fibres. The indoanilines formed from meta-phenylenediamines and from para-aminophenols in an alkaline oxidizing medium impart more or less purple red colours to keratinous fibres. Depending on the oxidation bases with which they are combined, meta-phenylenediamines can thus give red or blue colours, which are two fundamental colours in hair dyeing, and which are indispensable not only for obtaining blacks and greys but also coppery or ashen chestnut browns. The extremely important part played by meta-phenylenediamines in oxidation hair dyeing can thus be seen.

It is important, furthermore, that the oxidation dye precursors and the couplers which are employed in the oxidation dye compositions impart to hair, in an alkaline oxidizing medium, colours which are stable to light, to washing, to inclement weather and to perspiration. It is desirable that these colours should be unselective or relatively unselective, that is to say that the colours obtained on natural hair and on hair sensitized by a permanent wave or by a bleaching treatment should be substantially identical. It is also necessary that these compounds should have the benefit of a satisfactory harmlessness.

Many couplers of the type of meta-phenylenediamines substituted on the aromatic nucleus are already known. However, a large number of them do not satisfy the desired requirements.

The Applicant has just found that 2,4-diamino-1,3,5-trimethoxybenzene, which is a new compound, and its acid addition salts, satisfy all these requirements and may be advantageously employed as couplers in combination with other oxidation dye precursors and especially precursors of the para type.

The subject of the present invention is consequently 2,4-diamino-1,3,5-trimethoxybenzene of formula:

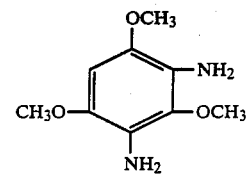

and its acid addition salts as new compounds, together with the process for their preparation and their use as couplers, in combination with oxidation dye precursors, for dyeing keratinous fibres and human hair in particular.

2,4-Diamino-1,3,5-trimethoxybenzene or one of its salts, combined with p-phenylenediamines in an alkaline oxidizing medium, endows hair with strong blue colours which are more or less rich in green or in purple.

When this coupler is combined with a p-aminophenols, in an alkaline oxidizing medium, it endows hair with red colours of good stability.

Another subject of the present invention is therefore a hair dyeing composition comprising, in a cosmetically acceptable aqueous substrate, 2,4-diamino-1,3,5-trimethoxybenzene or one of its acid addition salts, as a coupler, in combination with at least one oxidation dye precursor of the para type.

A further object of the invention consists of a process of hair dyeing employing the development by an oxidizing agent using composition such as defined above.

2,4-Diamino-1,3,5-trimethoxybenzene and its addition salts with an acid and in particular with an inorganic acid such as hydrochloric, hydrobromic or sulphuric acids, is prepared by catalytic reduction of 2,4-dinitro-1,3,5-trimethoxybenzene, which is a known compound, described in Beilstein 6 H 1106, EII 1079, EIII 6309, EIV 7372. The catalytic reduction is carried out under hydrogen pressure, in the presence of a catalyst such as palladium or nickel, deposited or undeposited on a substrate such as charcoal, calcium or barium carbonate, alumina or a silica gel, in a solvent consisting of water, a lower alcohol, a glycol or glycol ether, or a mixture of these compounds, at a temperature of between 50° C. and 200° C.

The oxidation hair dyeing compositions in accordance with the invention comprise, in a cosmetically acceptable aqueous substrate, 2,4-diamino-1,3,5-trimethoxybenzene or one of its acid addition salts, as a coupler, and at least one oxidation dye precursor of the para type.

The oxidation dye precursor of the para type is chosen from benzene-related or heterocyclic derivatives such as, for example, pyridine, to which two amino groups or an amino group and a hydroxyl group are attached in a para position. These oxidation dye precursors may be present in the dye compositions in the form of the free bases or in the form of acid addition salts.

The particularly preferred oxidation dye precursors which can be employed in accordance with the invention are chosen from the para-phenylenediamines corresponding to the general formula (II) below:

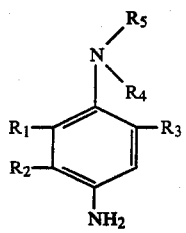

(II)

or the corresponding salts, in which formula $R_1$, $R_2$ and $R_3$ are identical or different and denote a hydrogen or halogen atom, an alkyl radical containing 1 to 4 carbon atoms or an alkoxy radical containing 1 to 4 carbon atoms, and $R_4$ and $R_5$ are identical or different and denote a hydrogen atom or an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, the alkyl or alkoxy groups denoted by $R_4$ and $R_5$ containing from 1 to 4 carbon atoms, or else $R_4$ and $R_5$, together with the nitrogen atom to which they are linked, may form a piperidino or morpholino heterocyclic ring, provided that $R_1$ or $R_3$ denote a hydrogen atom when $R_4$ and $R_5$ do not denote a hydrogen atom.

Among the compounds of formula (II) there may be mentioned: para-phenylenediamine, para-tolylenediamine, methoxy-para-phenylenediamine, chloro-para-phenylenediamine, 2,6-dimethyl-para-phenylenediamine, 2,5-methylpara-phenylenediamine, 2,3-dimethyl-para-phenylenediamine, isopropyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-di($\beta$-hydroxyethyl)paraphenylenediamine, 3-methyl-4-amino-N,N-di($\beta$-hydroxyethyl)aniline, 3-chloro-4-amino-N,N-di($\beta$-hydroxyethyl)aniline, 4-amino-N,N-(ethyl,carbamylmethyl)aniline, 3-methyl-4-amino-N,N-(ethyl,carbamylmethyl)aniline, 4-amino-N,N-(ethyl,$\beta$-piperidinoethyl)aniline, 3-methyl-4-amino-N,N-(ethyl,$\beta$-piperidinoethyl)aniline, 4-amino-N,N-(ethyl,$\beta$-morpholinoethyl)aniline, 3-methyl-4-amino-N,N-(ethyl,$\beta$-morpholinoethyl)aniline, 4-amino-N,N-(ethyl,$\beta$-acetylaminoethyl)aniline, 4-amino-N-$\beta$-methoxyethylaniline, 3-methyl-4-amino-N,N-(ethyl,$\beta$-acetylaminoethyl)aniline, 4-amino-N,N-(ethyl,$\beta$-mesylaminoethyl)aniline, 3-methyl-4-amino-N,N-(ethyl,$\beta$-mesylaminoethyl)aniline, 4-amino-N,N-(ethyl,$\beta$-sulphoethyl)aniline, 3-methyl-4-amino-N,N-(ethyl,$\beta$-sulphoethyl)aniline, N-[(4'-amino)phenyl]morpholine and N-[(4'-amino)phenyl]piperidine. These oxidation dye precursors of the para type may be introduced into the dye composition in the form of free base or in the form of cosmetically acceptable salts such as in hydrochloride, hydrobromide or sulphate form.

2,4-Diamino-1,3,5-trimethoxybenzene or its salts may also be employed with para-aminophenols to give shades which are particularly stable to light, to inclement weather and to washing after development in the presence of an oxidizing agent. Among para-aminophenols there may be mentioned: p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-($\beta$-hydroxyethyl)-4-aminophenol, 2-methoxy-4-aminophenol and 3-methoxy-4-aminophenol.

2,4-Diamino-1,3,5-trimethoxybenzene or its salts may also be employed with heterocyclic para oxidation dye precursors, among which there may be mentioned 2,5-diaminopyridine, 2-hydroxy-5-aminopyridine and tetraaminopyrimidine.

The dye compositions according to the invention may also contain oxidation dye precursors of the ortho type, such as ortho-aminophenols, ortho-phenylenediamines or ortho-diphenols. For example, 1-amino-2-hydroxybenzene, 6-methyl-1-hydroxy-2-aminobenzene and 4-methyl-1-amino-2-hydroxybenzene may be mentioned.

The dye compositions in accordance with the invention containing 2,4-diamino-1,3,5-trimethoxybenzene or its salts may optionally contain other couplers which are known per se, such as meta-diphenols, meta-aminophenols, meta-phenylenediamines, meta-acylaminophenols, meta-ureidophenols, meta-carbalkoxyaminophenols, $\alpha$-naphthol, and couplers containing an active methylene group such as $\beta$-ketonic compounds and pyrazolones.

By way of example, there may be mentioned, in particular: 2,4-dihydroxyphenoxyethanol, 2,4-dihydroxyanisole, meta-aminophenol, resorcinol, 4-chlororesorcinol, resorcinol monomethyl ether, 2-methyl-5-aminophenol, 2-methyl5-N-($\beta$-hydroxyethyl)aminophenol, 2-methyl-5-N-($\beta$-mesylaminoethyl)aminophenol, 2,6-dimethyl-3-aminophenol, 6-hydroxybenzomorpholine, 2,4-diaminophenoxyethanol, 6-aminobenzomorpholine, 2-[N-($\beta$-hydroxyethyl)amino-4-amino]-phenoxyethanol, 2-amino-4-N-($\beta$-hydroxyethyl)aminoanisole, (2,4-diamino)phenyl-$\beta$,$\gamma$-dihydroxypropyl ether, 2,4-diaminophenoxyethylamine, 3,4-methylenedioxyphenol, 3,4-methylenedioxyaniline and their salts.

Direct dyes such as azo or anthraquinone-based dyes or nitro derivatives of the benzene series may be added to these compositions in order to shade or to enrich in tints the colours contributed by the oxidation dye precursors, as is well known.

All the para compounds and couplers employed in the dye compositions in accordance with the invention preferably represent from 0.1 to 7% of the total weight of the said composition. The concentration of 2,4-diamino-1,3,5-trimethoxybenzene may vary between 0.05 and 3.5% of the total weight of the composition.

The cosmetically acceptable aqueous substrate has a pH which may vary between 8 and 11; it is preferably between 9 and 11.

It is adjusted to the desired value by means of an alkalifying agent such as aqueous ammonia, alkali metal carbonates or alkanolamines such as mono-, di- or triethanolamine.

In their preferred form of embodiment, the dye compositions in accordance with the invention also contain anionic, cationic, nonionic or amphoteric surface-active agents or mixtures thereof. Among these surface-active agents there may be more particularly mentioned: alkylbenzenesulphonates, alkylnaphthalenesulphonates, fatty alcohol sulphates, ether sulphates and sulphonates, quaternary ammonium salts such as trimethylcetylammonium bromide, cetylpyridinium bromide, optionally oxyethylenated fatty acid ethanolamides, polyoxyethylenated acids, alcohols and amines, polyglycerolated alcohols, polyoxyethylenated or polyglycerolated alkylphenols, and polyoxyethylenated alkyl sulphates.

The surface-active agents are present in the compositions in accordance with the invention in proportions of between 0.5 and 40% by weight, and preferably between 4 and 30% by weight relative to the total weight of the composition.

These compositions may also contain organic solvents for dissolving compounds which might not be sufficiently soluble in water. Among these solvents, there may be mentioned by way of example: lower $C_1$-$C_4$ alkanols such as ethanol and isopropanol, glycerol, glycols or glycol ethers such as 2-butoxyethanol, ethylene glycol, propylene glycol, diethylene glycol monoethyl ether and monomethyl ether, as well as similar products and mixtures thereof. The solvents are preferably present in a proportion of between 1 and 40% by weight, and in particular between 5 and 30% by weight relative to the total weight of the composition.

The thickening agents which may be added to the compositions in accordance with the invention are taken especially from the group consisting of sodium alginate, gum arabic, cellulose derivatives such as methyl cellulose, hydroxyethyl cellulose, hydroxypropyl cellulose, hydroxymethyl cellulose, carboxymethyl cellulose, acrylic acid polymers or xanthan gum. It is also possible to employ inorganic thickening agents such as bentonite. These thickening agents are preferably present in proportions of between 0.1 and 5% by weight, and in particular between 0.5 and 3% by weight relative to the total weight of the composition.

The compositions may contain antioxidant agents chosen in particular from sodium sulphite, thioglycolic acid, sodium bisulphite, ascorbic acid and hydroquinone. These antioxidant agents are present in the composition in proportions of between 0.05 and 1.5% by weight relative to the total weight of the composition.

Other adjuvants which may be employed in accordance with the invention are, for example, penetrating agents, sequestering agents, buffers and perfumes.

The dye compositions in accordance with the invention may be presented in various forms such as in the form of liquids, creams, gels or any other suitable form for effecting dyeing of keratinous fibres and especially of human hair. They may also be packaged in aerosol bottles in the presence of a propellant agent.

The dye compositions in accordance with the invention, containing an oxidation dye precursor of the para type and 2,4-diamino-1,3,5-trimethoxybenzene or one of its salts, are employed in a hair dyeing process using development with an oxidizing agent.

In accordance with this process, the dye composition described above is mixed at the time of use with a sufficient quantity of an oxidizing solution, and then the mixture obtained is applied to hair.

The oxidizing solution contains oxidizing agents such as hydrogen peroxide, urea peroxide or persalts such as ammonium persulphate. A 20-volume solution of hydrogen peroxide is preferably employed.

The mixture obtained is applied to hair; it is left in place for 10 to 40 minutes, preferably 15 to 30 minutes, after which the hair is rinsed, is washed with shampoo, is rinsed again and is dried.

Another process for using 2,4-diamino-1,3,5-trimethoxybenzene in accordance with the invention consists in dyeing hair using a process in a number of stages, according to which the oxidation dye precursor of the para type is applied by means of a composition as defined above, in a first stage, and, in a second stage, 2,4-diamino-1,3,5-trimethoxybenzene is applied. The oxidizing agent is present in the composition applied in the second stage or else is applied to the hair itself in a third stage, the conditions for leaving to act, for drying and for washing being identical with those indicated in the process above.

The examples below are used to better illustrate the invention, but are not intended to limit its scope in any way.

Preparation of 2,4-diamino-1,3,5-trimethoxybenzene dihydrochloride

A mixture consisting of 0.1 mole (25.8 g) of 2,4-dinitro-1,3,5-trimethoxybenzene, 120 ml of diethylene glycol dimethyl ether and 6 ml of water is heated in an autoclave at 80° C. for 1 hour in the presence of 4 g of palladium at a concentration of 10% on charcoal and under a hydrogen pressure (20 kg/cm$^2$).

The catalyst is removed by hot filtration of the reaction medium.

The expected product precipitates from the filtrate after the addition of 50 ml of concentrated hydrochloric acid. The product prepared in this manner is purified, after washing and drying hot under an air vacuum, by dissolving in 50 ml of boiling water, filtering the hot aqueous solution and precipitating by the addition of 100 ml of concentrated hydrochloric acid.

Analysis of the product obtained gives the following results:

| Analysis | Calculated for $C_9H_{16}N_2O_3Cl_2$ | Found |
| --- | --- | --- |
| C% | 39.85 | 39.82 |
| H% | 5.90 | 5.94 |
| N% | 10.33 | 10.20 |
| O% | 17.71 | 17.89 |
| Cl% | 26.20 | 26.29 |

Example of application 1

The following dye mixture is prepared:

| | |
| --- | --- |
| 2,4-Diamino-1,3,5-trimethoxybenzene dihydrochloride | 0.68 g |
| p-Phenylenediamine | 0.27 g |
| Oleyl alcohol polyglycerolated with 2 moles of glycerol | 4.5 g |
| Oleyl alcohol polyglycerolated with 4 moles of glycerol | 4.5 g |
| Ethomeen O 12 - Armour Hess Chemical Ltd (oleylamine oxyethylenated with 12 moles of EO) | 4.5 g |
| Comperlan KD - Henkel (copra diethanolamide) | 9 g |
| Propylene glycol | 4 g |
| 2-Butoxyethanol | 8 g |
| 96° ethanol | 6 g |
| Masquol DTPA - Protex (pentasodium salt of diethylenetriaminepentaacetic acid) | 2 g |
| Hydroquinone | 0.15 g |
| Sodium bisulphite solution, 35° Be | 1.3 g |
| Aqueous ammonia, 22° Be | 10 g |
| Water q.s. | 100 g |
| pH: 10 | |

100 g of 20-volume hydrogen peroxide are added at the time of use. The mixture, applied to bleached hair for 20 minutes at 35° C. imparts a dark purple blue colour to it after shampooing and rinsing.

Example of application 2

The following dye mixture is prepared:

| | |
|---|---|
| 2,4-Diamino-1,3,5-trimethoxybenzene dihydrochloride | 0.68 g |
| p-Tolylenediamine dihydrochloride | 0.49 g |
| Cemulsol NP 4 - Rhone-Poulenc (nonylphenol oxyethylenated with 4 moles of EO) | 12 g |
| Cemulsol NP 9 - Rhone-Poulenc (nonylphenol oxyethylenated with 9 moles of EO) | 15 g |
| Oleyl alcohol polyglycerolated with 2 moles of glycerol | 1.5 g |
| Oleyl alcohol polyglycerolated with 4 moles of glycerol | 1.5 g |
| Propylene glycol | 6 g |
| Trilon B (ethylenediaminetetraacetic acid) | 0.12 g |
| Aqueous ammonia, 22° Be | 11 g |
| Water q.s. | 100 g |
| pH: 8.6 | |

100 g of 20-volume hydrogen peroxide are added at the time of use. When applied to 90% naturally white hair for 20 minutes at 35° C., the mixture imparts a pure dark blue colour to it after shampooing and rinsing.

Example of application 3

The following dye mixture is prepared:

| | |
|---|---|
| 2,4-Diamino-1,3,5-trimethoxybenzene dihydrochloride | 0.68 g |
| 4-Amino-N—β-methoxyethylaniline dihydrochloride | 0.59 g |
| Carbopol 934 - Goodrich Chemicals (acrylic acid polymer with an MW of 2 to 3 million) | 3 g |
| Ethanol, 96° | 11 g |
| 2-Butoxyethanol | 5 g |
| Trimethylcetylammonium bromide | 2 g |
| Trilon B (ethylenediaminetetraacetic acid) | 0.2 g |
| Aqueous ammonia, 22° Be | 10 g |
| Sodium bisulphite, 35° Be | 1 g |
| Water q.s. | 100 g |
| pH: 9.7 | |

100 g of 20-volume hydrogen peroxide are added at the time of use. When applied to 90% naturally white hair for 20 minutes at 35° C., the mixture imparts a dark blue colour to it after shampooing and rinsing.

Example of application 4

The following dye mixture is prepared:

| | |
|---|---|
| 2,4-Diamino-1,3,5-trimethoxybenzene dihydrochloride | 0.68 g |
| p-Aminophenol | 0.27 g |
| Oleyl alcohol polyglycerolated with 2 moles of glycerol | 4.5 g |
| Oleyl alcohol polyglycerolated with 4 moles of glycerol | 4.5 g |
| Ethomeen O 12 - Armoon Hess Chemical Ltd (oleylamine oxyethylenated with 12 moles of EO) | 4.5 g |
| Comperlan KD - Henkel (copra diethanolamide) | 9 g |
| Propylene glycol | 4 g |
| 2-Butoxyethanol | 8 g |
| Ethanol, 96° | 6 g |
| Masquol DTPA - Protex (pentasodium salt of diethylenetriaminepentaacetic acid) | 2 g |
| Hydroquinone | 0.15 g |
| Sodium bisulphite solution, 35° Be | 1.3 g |
| Aqueous ammonia, 22° Be | 10 g |
| Water q.s. | 100 g |
| pH: 10 | |

100 g of 20-volume hydrogen peroxide are added at the time of use. When applied to 90 % naturally white hair for 20 minutes at 35° C., the mixture imparts a dark purple red colour to it after shampooing and rinsing.

EXAMPLE OF APPLICATION 5

The following dye mixture is prepared:

| | |
|---|---|
| 2,4-Diamino-1,3,5-trimethoxybenzene dihydrochloride | 0.68 g |
| 2-Methyl-4-aminophenyl | 0.31 g |
| Alfol C 16/18 - Condea (cetylstearyl alcohol) | 19 g |
| Eutanol G - Henkel (2-octyldodecanoyl) | 4.5 g |
| Mergital C.S. - Henkel (cetylstearyl alcohol with 15 moles of EO) | 2.5 g |
| Ammonium lauryl sulphate | 10 g |
| Cationic polymer containing the following repeat unit: 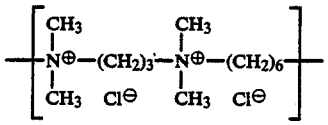 with a molecular weight of about 10,000 | 4 g |
| Benzyl alcohol | 2 g |
| Aqueous ammonia, 22° Be | 11 ml |
| Trilon B (ethylenediaminetetraacetic acid) | 1 g |
| Sodium bisulphite, 35° Be | 1.2 g |
| Water q.s. | 100 g |
| pH: 9.7 | |

100 g of 20-volume hydrogen peroxide are added at the time of use. When applied to 90% naturally white hair for 20 minutes at 35° C., the mixture imparts a red grey colour to it after shampooing and rinsing.

Example of application 6

The following dye mixture is prepared:

| | |
|---|---|
| 2,4-Diamino-1,3,5-trimethoxybenzene dihydrochloride | 0.1 g |
| para-Phenylenediamine | 0.08 g |
| para-Aminophenol | 0.16 g |
| Resorcinol | 0.13 g |
| meta-Aminophenol | 0.09 g |
| 2-Methyl-5-(β-hydroxyethyl)aminophenol | 0.1 g |
| Alfol C 16/18 - Condea (cetylstearyl alcohol) | 8 g |
| Lanette E Wax - Henkel (sodium cetylstearyl sulphate) | 0.5 g |
| Cemulsol B - Rhone-Poulenc (ethoxylated castor oil) | 1 g |
| Oleoyl diethanolamide | 1.5 g |
| Masquol DTPA - Protex (pentasodium salt of diethylenetriaminepentaacetic acid) | 2.5 g |
| Aqueous ammonia, 22° Be | 11 g |
| Water q.s. | 100 g |
| pH: 10.3 | |

100 g of 20-volume hydrogen peroxide are added at the time of use. When applied to permanent-waved hair for 20 minutes at 35° C., the mixture imparts a dark grey colour to it with a red tint, after shampooing and rinsing.

Example of application 7

The following dye mixture is prepared:

| | |
|---|---|
| 2,4-Diamino-1,3,5-trimethyoxybenzene dihydrochloride | 1.35 g |
| N,N—Di(β-hydroxyethyl)-para-phenylenediamine dihydrochloride | 1.34 g |
| Alfol C 16/18 - Condea (cetylstearyl alcohol) | 19 g |

-continued

| | |
|---|---|
| Eutanol G - Henkel (2-octyldodecanol) | 4.5 g |
| Mergital C.S. - Henkel (cetylstearyl) alcohol with 15 moles of EO) | 2.5 g |
| Ammonium lauryl sulphate | 10 g |
| Cationic polymer containing the following repeat unit: | 4 g |
| 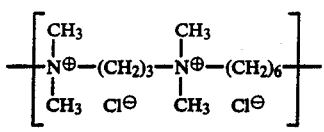 | |
| with a molecular weight of about 10,000 | |
| Benzyl alcohol | 2 g |
| Aqueous ammonia, 22° Be | 11 ml |
| Trilon B (ethylenediaminetetraacetic acid) | 1 g |
| Sodium bisulphite, 35° Be | 1.2 g |
| Water q.s. | 100 g |
| pH: 9.4 | |

100 g of 20-volume hydrogen peroxide are added at the time of use. When applied to 90% naturally white hair for 15 minutes at 35° C., the mixture imparts an ocean blue colour to it after shampooing and rinsing.

We claim:

1. 2,4-Diamino-1,3,5-trimethoxybenzene of formula:

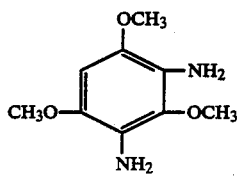 (I)

and acid addition salts thereof.

2. Process for the preparation of 2,4-diamino-1,3,5-trimethoxybenzene and of acid addition salts thereof, which consists in performing a catalytic reduction of 2,5-dinitro-1,3,5-trimethoxybenzene under hydrogen pressure, in the presence of a catalyst such as palladium or nickel, deposited or undeposited on a substrate such as charcoal, calcium or barium carbonate, alumina or a silica gel, in a solvent consisting of water, a lower alcohol, a glycol or glycol ether or a mixture of these compounds, at a temperature of between 50° C. and 200° C.

3. A keratinous dye composition comprising 2,4-diamino-1,3,5-trimethoxybenzene or of acid addition salts thereof as a coupler, in combination with oxidation dye precursors of the para type.

4. A keratinous fiber dye composition which contains 2,4-diamino-1,3,5-trimethoxybenzene or an acid addition salt thereof as a coupler, in combination with at least one oxidation dye precursor of the para type. which contains 0.05 to 3.5% by weight of 2,4-diamino-1,3,5-trimethoxybenzene or of one of its acid addition salts, based on the total weight of the composition.

5. The dye composition according to claim 4, wherein the oxidation dye precursor of the para type is chosen from the group consisting of para-phenylenediamines, para-aminophenols, heterocyclic para compounds and mixtures thereof.

6. The dye composition according to claim 5, wherein the para-phenylenediamines correspond to the formula:

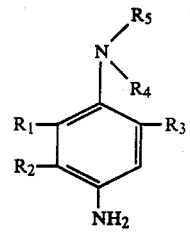 (II)

in which $R_1$, $R_2$ and $R_3$ are identical or different and denote a hydrogen or halogen atom, an alkyl radical containing 1 to 4 carbon atoms or an alkoxy radical containing 1 to 4 carbon atoms, and $R_4$ and $R_5$ are identical or different and denote a hydrogen atom or an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, the alkyl or alkoxy groups denoted by $R_4$ and $R_5$ containing from 1 to 4 carbon atoms, or else $R_4$ and $R_5$, together with the nitrogen atom to which they are linked, form a piperidino or morpholino heterocyclic ring provided that $R_1$ or $R_3$ denote a hydrogen atom when $R_4$ and $R_5$ do not denote a hydrogen atom, or consists of the salts of the compounds of formula (II) above.

7. The dye composition according to claim 6, which contains at least one para-phenylene diamine chosen from the group consisting of para-phenylenediamine, para-tolylenediamine, methoxy-para-phenylenediamine, chloro-para-phenylenediamine, 2,6-dimethyl-para-phenylenediamine, 2,5-dimethylpara-phenylenediamine, 2,3-dimethyl-para-phenylenediamine, isopropyl-para-phenylenediamine, 2-methyl-5-methoxy-paraphenylenediamine, 2,6-dimethyl-5-methoxy-para-phenylenediamine, N,N-dimethyl-para-phenylenediamine, 3-methyl-4-amino-N,N-diethylaniline, N,N-di(β-hydroxyethyl)paraphenylenediamine, 3-methyl-4-amino-N,N-di(β-hydroxyethyl)aniline, 3-chloro-4-amino-N,N-di(β-hydroxyethyl)aniline, 4-amino-N,N-(ethyl,carbamylmethyl)aniline, 3-methyl-4-amino-N,N-(ethyl,carbamylmethyl)aniline, 4-amino-N,N-(ethyl,β-piperidinoethyl)aniline, 3-methyl-4-amino-N,N-(ethyl,β-piperidinoethyl)aniline, 4-amino-N,N-(ethyl,β-morpholinoethyl)aniline), 3-methyl-4-amino-N,N-(ethyl,β-morpholinoethyl)aniline, 4-amino-N,N-(ethyl,β-acetylaminoethyl)aniline, 4-amino-N-β-methoxyethylaniline, 3-methyl-4-amino-N,N-(ethyl,β-acetylaminoethyl)aniline, 4-amino-N,N-(ethyl,β-mesylaminoethyl)aniline, 3-methyl-4-amino-N,N-(ethyl-β-mesylaminoethyl)aniline, 4-amino-N,N-(ethyl, β-sulphoethyl)aniline, 3-methyl-4-amino-N,N-(ethyl,β-sulphoethyl)aniline, N-[(4'-amino)phenyl]morpholine and N-[(4'-amino)phenyl]piperidine, in the form of free base or in the form of cosmetically acceptable salts.

8. The dye composition according to claim 5, which contains at least one para-aminophenol chosen from the group consisting of para-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl)-4-aminophenol, 2-methoxy-4-aminophenol and 3-methoxy-4-aminophenol.

9. The dye composition according to claim 5, wherein the oxidation dye precursor of the para type is a heterocyclic para compound chosen from 2,5-diaminopyridine, 2-hydroxy-5-aminopyridine and tetraaminopyridine.

10. The dye composition according to claim 4, which contains other couplers chosen from the group consisting of meta-diphenols, meta-aminophenols, meta-phenylenediamines, meta-acylaminophenols, meta-ureidophenols, meta-carbalkoxyaminophenols, α-naphthol, β-ketonic compounds and pyrazolones.

11. The dye composition according to claim 4, wherein the total concentration of couplers and of oxidation dye precursors of the para type is between 0.1 and 7% by weight.

12. The dye composition according to claim 4 which additionally contains dye precursors of the ortho type chosen from the group consisting of ortho-aminophenols, orthophenylenediamines and ortho-diphenols.

13. The dye composition according to claim 4, which additionally contains direct dyes chosen from the group consisting of azo and anthraquinone dyes and nitro derivatives of the benzene series.

14. The dye composition according to claim 4, which has a pH of between 8 and 11.

15. The dye composition according to claim 4, which contains 1 to 40% by weight of an organic solvent chosen from the group consisting of lower alkanols, glycerol, glycols or glycol ethers, and mixtures thereof.

16. The dye composition according to claim 4, which additionally contains 0.5 to 40% by weight of at least one anionic, cationic, non-ionic or amphoteric surface-active agent or mixtures thereof.

17. The dye composition according to claim 4, which additionally contains cosmetic adjuvants chosen from the group consisting of thickeners, antioxidant agents, penetration agents, sequestering agents, buffers, perfumes, alkalifying agents and propellants.

18. The hair dyeing process comprising in sequence the steps of
(a) mixing a dye composition according to claim 4 with an oxidizing solution,
(b) applying to the hair the resulting composition from step a),
(c) permitting said composition from step (a) to remain in contact with the hair for a period ranging from about 10 to about 40 minutes to form a dye on the hair; then
(d) rinsing,
(e) shampooing, and
(f) drying the dyed hair.

19. The hair dyeing process comprising in sequence the steps of
(a) applying to the hair a dyeing composition containing at least one oxidation dye precursor of the para type as defined in claim 5;
(b) applying a dye composition containing 2,4-diamino-1,3,5-trimethoxybenzene or an acid addition salt thereof and an oxidizing agent;
(c) permitting said compositions from step (a) and and step b) to remain in contact with the hair for a period ranging from about 10 to about 40 minutes to form a dye on the hair; then
(d) rinsing;
(e) shampooing; and
(f) drying the dyed hair.

20. The hair dyeing process comprising in sequence the steps of:
(a) applying to the hair a dyeing composition containing at least one oxidation dye precursor of the para type as defined in claim 5;
(b) applying a dye composition containing 2,4-diamino-1,3,5-trimethoxybenzene or an acid addition salt thereof;
(c) applying to the hair an oxidizing agent;
(d) permitting said compositions from step a) and step (b) and step c) to remain in contact with the hair for a period ranging from about 10 to about 40 minutes to form a dye on the hair; and
(e) rinsing;
(f) shampooing; and
(g) drying the dyed hair.

21. The dye composition according to claim 4, which has a pH of between 9 and 11.

* * * * *

UNITED STATES PATENT AND TRADEMARK OFFICE
CERTIFICATE OF CORRECTION

PATENT NO. : 4,891,045

DATED : Jan. 2, 1990

INVENTOR(S) : JUNINO et al

It is certified that error appears in the above-identified patent and that said Letters Patent is hereby corrected as shown below:

On the title page:

The filing date should read --June 27, 1988--.

Signed and Sealed this

Eighteenth Day of June, 1991

Attest:

HARRY F. MANBECK, JR.

Attesting Officer

Commissioner of Patents and Trademarks